(12) United States Patent
Sakas et al.

(10) Patent No.: US 7,639,895 B2
(45) Date of Patent: Dec. 29, 2009

(54) REGISTERING ULTRASOUND IMAGE DATA AND SECOND IMAGE DATA OF AN OBJECT

(75) Inventors: Georgios Sakas, Darmstadt (DE); Marcus Grimm, Egelsbach (DE)

(73) Assignee: Medcom Gesellschaft fur Medizinische Bildverarbeitung mbH, Darmstadt (DE)

( * ) Notice: Subject to any disclaimer, the term of this patent is extended or adjusted under 35 U.S.C. 154(b) by 666 days.

(21) Appl. No.: 11/539,318

(22) Filed: Oct. 6, 2006

(65) Prior Publication Data
US 2007/0083117 A1    Apr. 12, 2007

(30) Foreign Application Priority Data
Oct. 6, 2005    (EP)    ................... 05109289

(51) Int. Cl.
*G06K 9/36*    (2006.01)
(52) U.S. Cl. .................. 382/284; 382/128; 382/282
(58) Field of Classification Search ................ 382/128, 382/130, 131, 132, 278, 282, 284
See application file for complete search history.

(56) References Cited

U.S. PATENT DOCUMENTS

| 6,425,867 B1 * | 7/2002 | Vaezy et al. | 600/439 |
| 6,591,130 B2 * | 7/2003 | Shahidi | 600/424 |
| 6,716,184 B2 * | 4/2004 | Vaezy et al. | 601/3 |
| 6,892,090 B2 * | 5/2005 | Verard et al. | 600/424 |

FOREIGN PATENT DOCUMENTS

EP    1124201    8/2001

OTHER PUBLICATIONS

Oct. 14, 2000, Gobbi et al., "Ultrasound/MRI overlay with image warping for neurosurgery" Lecture Notes in Computer Science, Springer Verlag, New York, NY, vol. 1935, pp. 106-114.
Jul. 1997, Foley et al., "Computer Graphics: Principles amd practice" Addison-Wesley, pp. 92-99.

(Continued)

*Primary Examiner*—Yosef Kassa
(74) *Attorney, Agent, or Firm*—Neifeld IP Law, PC (57) ABSTRACT

The invention relates to a method of registering ultrasound image data of an object and second image data of the object, wherein the second image data are three-dimensional (3-D) image data. Sets (first sets IUS) of the ultrasound image data are obtained, wherein each set of ultrasound image data consists of ultrasound image data of locations within a single plane of a coordinate system of the ultrasound image data. Sets (second sets IEX) of 2-D image data from the second image data are extracted, wherein each set of 2-D image data consists of image data of locations within a single cut plane of a coordinate system of the second image data (unit 41). One of the first sets (IUS) is compared with one of the second sets (IEX) and a measure of similarity between the first set (IUS) and the second set (IEX) is automatically generated (unit 42). The similarity is optimised by varying the first set (IUS) and/or the second set (IEX) to be compared (unit 43).

7 Claims, 5 Drawing Sheets

OTHER PUBLICATIONS

Dec. 31, 1999, Pagoulatos et al., "Interactive 3D registration of ultrasound and magnetic resonance images based on a magnetic position sensor", IEEE Transactions on Information Technology in Biomedicine, IEEE Service Center, Los Alamitos, CA, vol. 3, No. 4, pp. 278-288.

Sep. 19, 1999, Gobbi et al., "Ultrasound probe tracking for real-time ultrasound/MRI overlay and visualization of brain shift" Medical Image Computing and Computer-assisted intervention. MICCAI International Conference Proceedings, pp. 920-927.

Sep. 19, 1999, Ionescu et al., "Automated registration of ultrasound with CT images: application to computer assisted prostate radiotherapy and orthopedics" Medical Image Computing and Computer-Assisted Intervention—MICCAI '99, Cambridge, UK, vol. 1679, pp. 768-777.

* cited by examiner

REGISTERING ULTRASOUND IMAGE DATA AND SECOND IMAGE DATA OF AN OBJECT

This application is claims priority to European patent application No. 05 109 289.8 filed on Oct. 6, 2005, and the contents of that application are incorporated herein by reference.

DESCRIPTION

The invention relates to a method and an arrangement of/for registering ultrasound image data of an object and second image data of the object, wherein the second image data are three-dimensional image data.

An ultrasound (US) detector may generate the first image data of the object and the second image data of the object are generated separately. For example, the second image data may have been recorded earlier by a computer tomography (CT), a magnetic resonance (MR), a positron emission tomography (PET), an X-ray and/or a three-dimensional (3D) US imaging device. Any type of 3-D image information can be used as the second image data. A combination device may combine the US and second image data of the object. The combined image data can be displayed in separate areas of a screen and/or may be superimposed on a screen. More particularly, the invention may be applied in the field of stereographic diagnosis concerning human or animal bodies, but also concerning material research and/or material examination.

Ultrasound detectors are comparatively easy to handle and are able to deliver image information quasi-continuously and, approximately, in real-time. However, in many applications, other imaging technologies (such as the ones mentioned above) provide better results in terms of resolution and clarity of image. Therefore, it has been proposed to combine image information of better quality, which has been recorded earlier, with real-time ultrasound image information. One precondition for combining is that the two types of image data are registered, i.e. their coordinate systems or spaces can be transformed into each other or into a common coordinate system. In other words: The term "register" means that the geometries of the two coordinate systems are brought into a defined relation.

In the scientific publication of Pagoulatos et al.: "Interactive 3-D Registration of Ultrasound and Magnetic Resonance Images Based on a Magnetic Position Sensor", published in IEEE TRANSACTIONS ON INFORMATION TECHNOLOGY IN BIOMEDICINE, VOL. 3, NO. 4, December 1999, an apparatus of the type mentioned above is described. A method is described to register the imaging object relative to an MR imaging device. The apparatus comprises a position sensor, which is firmly coupled to an ultrasound probe. Using the position sensor and due to the fact that its relative position to the ultrasound probe does not vary, it is possible to track the position and the orientation of the ultrasound probe. However, it is necessary to calibrate the position sensor relative to the ultrasound probe and to register the imaging object relative lo the coordinate system of the ultrasound probe.

The registration process of Pagoulatos is performed interactively. Specially designed landmarks (fiducials) are used to register the coordinate system of the MR data on one hand and a stationary coordinate system in which the object rests on the other hand. Several 3-D coordinates of the fiducials are interactively determined in the two coordinate systems.

According to another approach, the skull of the patient is used as a reference during the process of registering the US coordinate system and the coordinate system of the 3-D image data.

According to yet another approach, landmarks in the interior of the patient may be used for the registration.

Using systems of the type described before, it is possible to display MR image information of the same orientation and/or scaled in the same manner as the most recent US image. It can be simulated that the MR image is recorded in (near) real-time, provided that the image data processing is fast enough.

However, the various calibration and registration procedures are time-consuming and need to be performed with care in order to obtain good results. For example, the position of a set of landmarks on the surface of the object and/or anatomical markers (in case of a human or animal body) is to be detected during registration. This requires time and expertise. Furthermore, it might be difficult to find and identify a sufficient number of landmarks which are suitable to complete the process of registration.

Furthermore, modern US systems enable the user to vary the penetration depth of the US image in the object and/or to change the ultrasound probe. As a consequence, the registration of the imaging object relative to the coordinate system of the ultrasound probe is no longer valid.

It is an object of the present invention to provide an apparatus and a method of the type indicated above such that the registration of the US data on one hand and the 3-D image data on the other hand can be performed with high precision, within a short period of time and with a minimum of expertise.

It is proposed to automatically register the ultrasound image data and the second image data. In particular based on existing, preliminary registration information, 2-D image information is extracted from the second image data. The extracted 2-D image information corresponds (in particular in accordance with the registration information) to a two-dimensional area of the ultrasound image data. In particular, the extracted 2-D image information may correspond to a single two-dimensional ultrasound image. The extracted information is compared with two-dimensional ultrasound information. For example, the two-dimensional area of the ultrasound information is defined by the plane in which ultrasound waves of a 2-D ultrasound probe penetrate the body of the patient at a given scan position relative to the body. By comparing the two types of information, their similarity (or non-similarity) can be determined and by varying the relative position and/or relative orientation of the two data sets and by repeating the process, the images having the greatest similarity can be found. These images are images of the same two-dimensional areas of the object, wherein the orientation of the areas is the same, and, therefore, the images correspond to or define the correct registration.

Before the correct registration information is found, preliminary registration information can be used to extract the 2-D information from the 3-D image data. A cut plane of the coordinate system of the second image data may be chosen to be equal to the plane of the ultrasound coordinate system, wherein "equal to" is based on instantaneous values of the registration information. These instantaneous values may be updated during the process of optimising the similarity.

Due to the automatic registration, a minimum of expertise is required. Compared to interactive methods, the registration is more precise. The present invention does not rely on internal or external markers. Rather, the whole image information of the data sets, which are to be compared, can be used in the step of determining the similarity. There is no need for image information of a special type, such as a line or bifurcation, which can be recognised by a user or by a specially trained system. However, such special type of information can be part of the image data and will be evaluated if present.

In particular, the following is proposed: A method of registering ultrasound image data of an object and second image data of the object, wherein the second image data are three-dimensional image data and wherein the method comprises the steps:

obtaining sets (first sets) of the ultrasound image data, wherein each set of ultrasound image data consists of ultrasound image data of locations within a single plane of a coordinate system of the ultrasound image data (ultrasound coordinate system);

extracting sets (second sets) of 2-D image data from the second image data, wherein each set of 2-D image data consists of image data of locations within a single cut plane of a coordinate system of the second image data;

comparing one of the first sets with one of the second sets and automatically generating a measure of similarity between the first set and the second set; and optimising the similarity by (if necessary repeatedly) varying the first set and/or the second set to be compared.

"Varying the first set and/or the second set" means that a different data set is obtained or different data sets are obtained. This can be done, for example, by choosing a different ultrasound dataset and/or by extracting a different set of 2-D image data from the second image data. Furthermore, at least one of the sets can be varied by rotating and/or shifting the plane or cut plane of the data set. As a result, the various data sets may differ by the position of the respective plane or cut plane, by the orientation of the plane or cut plane, or both.

Preferably, the whole process, which comprises the steps of obtaining data sets of the ultrasound image data, of extracting data sets of the second image data, of generating a measure of similarity and of optimising the similarity (so that corresponding optimised registration information can be obtained), is performed fully automatically, e.g. by a computer or computer system. No user action is required. However, there is the option that a user inputs information which is used in the process. For example, the user may select a geometrical area of interest, such as a part of the area for which ultrasound image information is output by the ultrasound probe.

The step of comparing one of the first sets with one of the second sets and of generating the measure of similarity can be performed in different manners. For example, the differences between the image values (such as grayscale values) of the two data sets can be calculated (so called differential image) and the sum (or sum of the squares, or the like) of the differences can serve as the measure of similarity. However, according to the preferred embodiment of the invention, the mutual information of the first set and of the second set is determined. The mutual information is defined as that information, which one set contains about the other. The use of mutual information is known in the art of medical imaging, though not in the context of registering 2-D US and other 3-D information. In addition, maximising the mutual information of two different image entities for example MR image data and individual x-ray images using digitally reconstructed radiographs of the MR image data) is also known in the art. Equivalent to the problem of maximising the mutual information is minimizing the conditional entropy. The latter is an alternative method for the step of optimising the similarity.

It should be noted that digitally reconstructed radiographs (DRRs) are not the same as the 2-D sets which have been extracted from that the second image data. DRRs simulate an x-ray image by combining (for each pixel) image information along a direction which extends perpendicularly to the image plane. In contrast to this, the extracted 2-D sets comprise (for each pixel) image information only which is the image information of the location in the image plane.

In the step of optimising the similarity, different approaches can be applied in combination or only one of these approaches can be followed. For example, a Downhill Simplex algorithm may be used to find the minimised negative similarity (i.e. the maximised similarity), wherein the relative position and relative orientation of the ultrasound coordinate system and the coordinate system of the second image data may be the parameters to be varied.

Preferably, registration information, which defines a registration of the ultrasound coordinate system and of the coordinate system of the second image data, is determined according to an optimised pair of data sets, wherein the optimised pair comprises the first set and the second set having an optimum similarity. For example, the optimised registration information is then output to a system which combines (see above) and displays the ultrasound image data and the second image data.

The basic principles of obtaining registration information (in particular a registration matrix) are well known in the art (see for example the publication of Pagoulatos and the references cited therein) and need not be explained in more detail here.

According to a particularly preferred embodiment, a plurality of pairs of data sets are compared in the step of comparing and a measure of similarity is calculated for each of the pairs. Each of these pairs comprises one of the first sets and one of the second sets, wherein all of the pairs correspond to the same geometrical transformation for transforming the ultrasound coordinate system into the coordinate system of the second image data, or vice versa (i.e. transforming the second image data). The measures of similarity of all of the pairs are combined and the combined measure (i.e. the sum) is optimised by varying the first sets of the pairs and/or the second sets of the pairs in a geometrically corresponding manner.

For example, a user acquires a plurality of two-dimensional ultrasound images by scanning a region of interest. The corresponding movement of the ultrasound probe is tracked so that all of the two-dimensional images can be assigned to the same coordinate system, e.g. the coordinate system of the patient's body or of the tracking system. Then, for each of the ultrasound images, a corresponding image is extracted from the second image data and the similarity of all of the pairs is determined and used for optimisation. One advantage of the plurality of pairs is that the image information which can be evaluated during optimisation is increased.

Preferably, at least two of the ultrasound image data sets consist of image information of locations in (in each case one of) two different planes, wherein the two planes intersect each other at a common straight line. Experiments have confirmed that this approach accelerates the optimisation. Alternatively, the locations of the different images may be located in parallel planes. In addition, more than two US image data sets can be used, wherein some of the planes may be parallel and some not.

Preferably, a plurality of locations of the 2-D image data is determined in the step of extracting at least one of the second sets. The locations are located in a straight line in the cut plane, between end locations of the straight line, which define end points of the straight line at opposite ends. The end locations may be determined by transforming corresponding locations in the ultrasound coordinate system into the coordinate system of the second image data. Furthermore, the locations may be determined between the opposite end locations in consecutive order along the straight line.

This "scanline" procedure yields particularly fast extraction results.

Furthermore, an arrangement is provided for registering ultrasound image data of an object and second image data of the object, wherein the second image data are three-dimensional image data and wherein the apparatus comprises:

a data storage for storing the second image data and/or an interface for receiving the second image data; and a registration device which is adapted to register the ultrasound image data and the second image data.

The registration device comprises:

a dataset extraction unit which is adapted to extract sets of 2-D image data from the second image data, wherein each set of 2-D image data consists of image data of locations within a single cut plane of a coordinate system of the second image data;

a dataset comparison unit which is connected to the dataset extraction unit and which is adapted to compare at least one of the sets of 2-D image data with at least one set of ultrasound image data, wherein each set of ultrasound image data consists of ultrasound image data of locations within a single plane of a coordinate system of the ultrasound image data; and an optimisation unit which is connected to or part of the dataset comparison unit and which is adapted to optimise registration information, wherein the registration information is based on a comparison result of the dataset comparison unit.

Part of the arrangement of the whole arrangement may be realised using a computer or a computer system. In particular, the method according to the present invention may be implemented in software and/or hardware. Furthermore, the present invention includes:

a computer loadable data structure that is adapted to perform the method according to one of the embodiments described in this description while being executed on a computer or computer system, a computer program, wherein the computer program is adapted to perform the method according to one of the embodiments described in this description while being executed on a computer or computer system, a computer program comprising program means for performing the method according to one of the embodiments described in this description while the computer program is being executed on a computer or on a computer network, a computer program comprising program means according to the preceding item, wherein the program means are stored on a storage medium readable to a computer, a storage medium, wherein a data structure is stored on the storage medium and wherein the data structure is adapted to perform the method according to one of the embodiments described in this description after having been loaded into a main and/or working storage of a computer or of a computer network, and a computer program product having program code means, wherein the program code means can be stored or are stored on a storage medium, for performing the method according to one of the embodiments described in this description, if the program code means are executed on a computer or on a computer network.

Preferred embodiments and other examples of the invention will be described with reference to the accompanying drawing in the following. The figures of the drawing schematically show.

Figure 5:
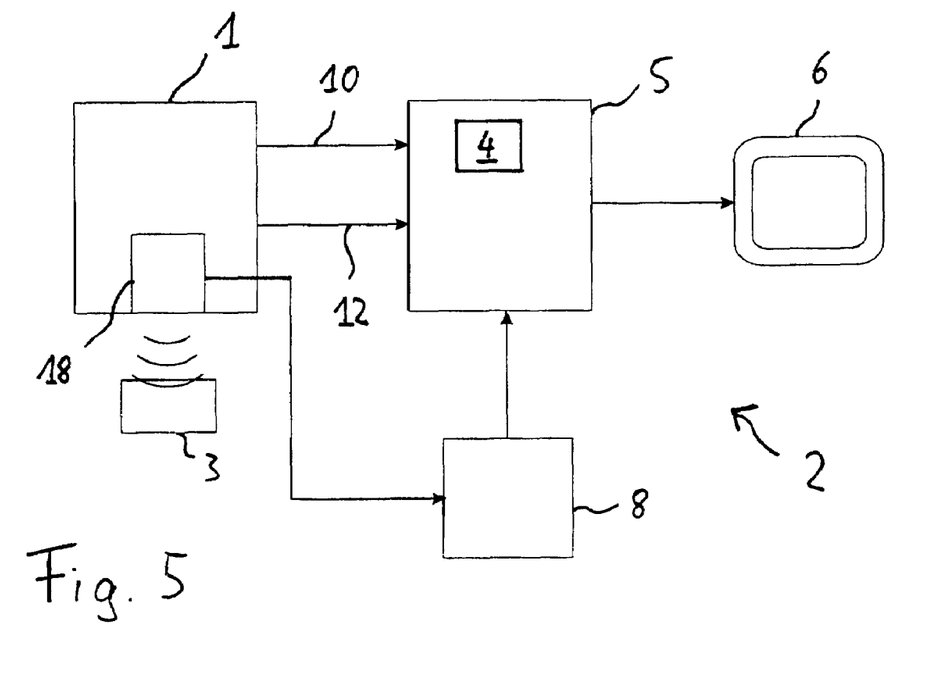
FIG. 5 an arrangement comprising an apparatus for combining ultrasound image data with a second type of data, e.g. CT image data.

For many different applications in medicine, it is desired to display images of an object 3 (such as part of a patient) on a screen. FIG. 5 shows an arrangement 2 which can be used for combining and displaying image data of different entities on a screen 6. An ultrasound detector 1 generates first image data of the object 3 and transfers the first image data to a combination device 5 via an image data connection 10. The combination device 5 comprises a data storage 4, which contains second image data that have previously been generated by a separate device (not shown in FIG. 5). The combination device 5 is adapted to combine the first and second image data and to display them on a screen 6, which is connected to the combination device 5. For example, the first and second image data may be displayed separately on a split screen or may be superimposed. In any case, it is preferred that a first image, which is generated using the first (US) image data, and a second image, which is generated using the second image data, precisely show at least partially the same area or region of the object 3 in the same orientation (angle of view) and scaling (dimensions). This requires registration of the coordinate systems of the two different image entities. When the registration has been completed, the movement of the ultrasound detector 1 in the coordinate system of the US image space (which is the system of the object as long as the US images are taken) can be tracked and the registration is still valid. This means, that the US images which will be taken in the following period of time can be combined with the 3-D images, using the same registration information.

The ultrasound detector 1 and the combination device 5 are connected to each other by an additional data connection 12 for transferring geometry data from the ultrasound detector 1 to the combination device 5. In particular, the geometry data connection 12 may be connected to a control unit of the ultrasound detector 1.

An ultrasound probe of the ultrasound detector 1 is firmly coupled to a position sensor 18 of a tracking system. The determination of the orientation and the location of such a position sensor and, thereby, of the ultrasound probe is known in the art (see the above-cited publication of Pagoulatos et al.). For example, magnetic and/or optical (e.g. infrared) signals may be used by the tracking system. The position sensor 18 is connected to a tracking system control unit 8 and the control unit 8 is connected to the combination device 5. During operation of the arrangement 2, the control unit 8 repeatedly or quasi-continuously transfers information concerning the position and concerning the orientation of the ultrasound probe 16 to the combination unit 5. Alternatively, this information may be transferred from the US detector to the combination device. I.e. this information might be at least partially included in the geometry data, which are transferred.

Figure 2:
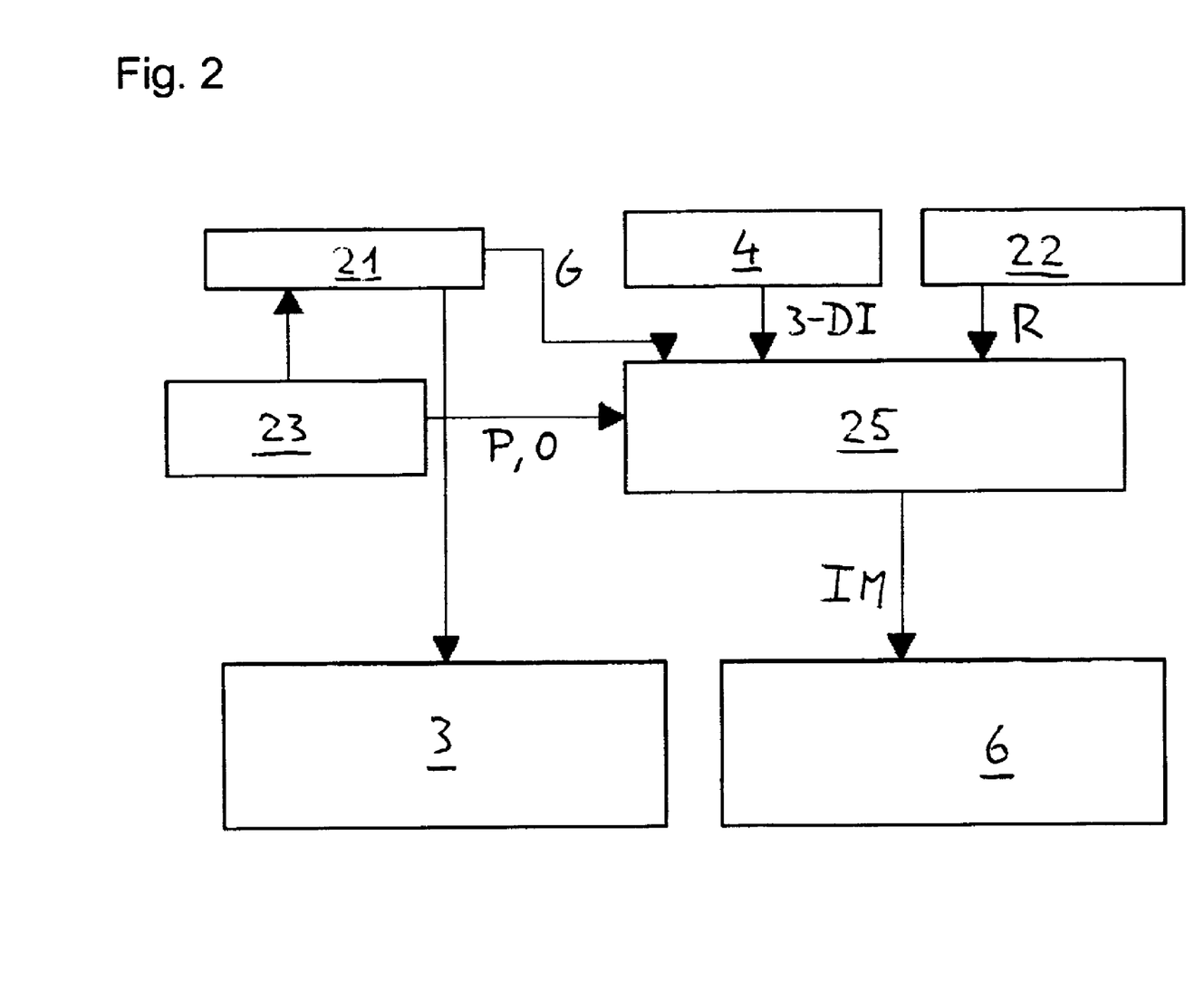
FIG. 2 an arrangement for registering the US data and the second image data.

The arrangement shown in FIG. 2 can be, for example, part of the arrangement of FIG. 5. An ultrasound generator 21 generates ultrasound signals which are emitted into the object 3. Echoes of the signals are detected and are used for the generation of the ultrasound images by the ultrasound detector 23 which is firmly coupled to the tracking sensor. Information about the current position P and orientation O of the ultrasound detector 23 is transferred from the ultrasound detector 23 to a registration device 25. In addition, geometry data G (in particular information about the scale and/or resolution of the current ultrasound image as well as information about a reference point in the ultrasound image, such as the so-called near point) are transferred from the ultrasound generator 21 to the registration device 25 (which optionally assigns the geometry data G and/or the current position P and orientation O to the respective image). Typically, the ultrasound generator 21 is integrated in the ultrasound detector 23. The registration device 25 may be part of the computer which comprises the combining device 5.

Furthermore, 3-D image information 3-DI (such as the second image data which is to be combined with the ultrasound image data) is transferred from the data storage 4, and/or via a data interface, to the registration device 25. A registration unit 22, which is adapted to store and/or to calculate (based on additional input information concerning the geometry of the arrangement 2 and concerning a geometry of an arrangement for generating the 3-D image information) registration information R, is connected to the registration device 25 and transfers the registration information R thereto. Having completed the registration process, which will be described in the following, the registration device 25 may output an image IM to the screen 6, wherein the image IM is a 2-D image which has been extracted from the second image data and which is registered with a corresponding ultrasound image. The ultrasound image may be transferred from the registration device 25 to the screen 6 as well.

Figure 1:
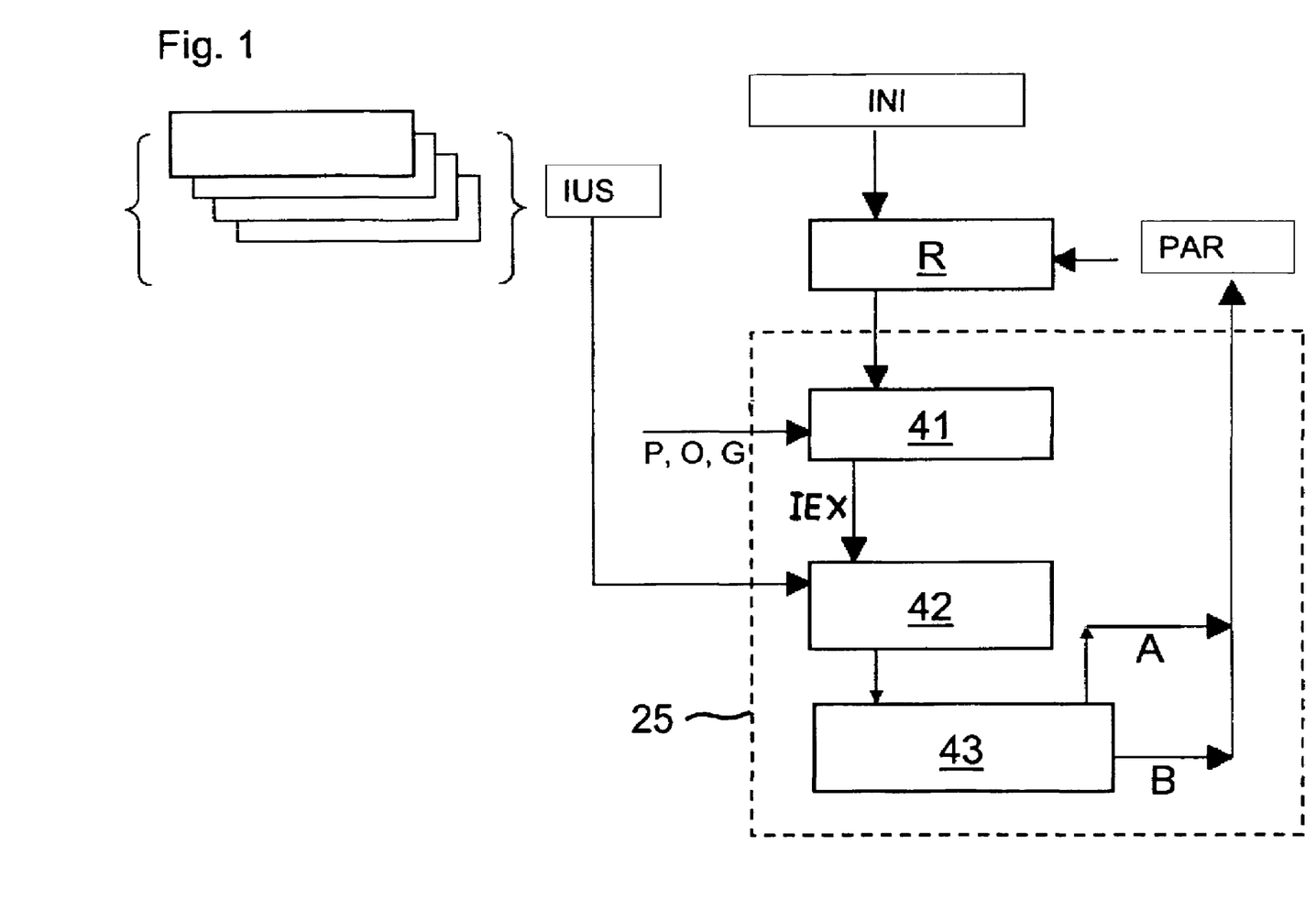
FIG. 1 a method of registering ultrasound image data and second image data according to the most preferred embodiment of the present invention.

The preferred Embodiment of the method is now described with reference to FIG. 1. A number of N (N is a positive integer greater than 1) US images IUS are generated by the ultrasound detector (top left area of the figure). For example, N is (greater than or equal to 5. Preferably N is greater than or equal to 10. Corresponding information P, O about the position and orientation of the ultrasound detector for each of the US images as well as geometry information G as mentioned above is transferred to a dataset extraction unit 41. The extraction unit 41 is adapted to extract 2-D image data sets from the second image data based on the information P, O, G and based on current values of registration information R (such as a registration matrix). Corresponding to the N US images IUS, N extracted images IEX are generated by unit 41 and are transferred to data set comparison unit 42.

The registration information R is optimised, as will be described in the following. At the beginning of the optimisation process, initial values INI of the registration information R are input to the process. Optionally, the initial values INI may be varied before the optimisation (e.g. using a downhill simplex algorithm) is carried in order to obtain better initial values. For example, the initial values INI may be stochastically varied and the set of values is taken as initial values for which the similarity is the highest. This means that the loop described below can be executed for each of the sets of initial values.

The data set comparison unit 42 compares N pairs of data sets, each of which is formed by ore of the N extracted 2-D image data sets and by a corresponding one of the N ultrasound images IUS and calculates a value of the similarity (for example: the mutual information) of the two sets for each pair. The similarity values of the N sets are combined (for example: the sum of the values is calculated) and the result is output to an optimisation unit 43. Units 41, 42, 43 may be part of the registration device 25 of FIG. 2.

The optimisation unit 43 determines whether the combined similarity is better than for a previous cycle of the optimisation process. If yes (path A), the current values of the registration information are saved. If no (path B), previously saved values or the registration information are kept as current values.

If the optimisation process has not been finished, information concerning the variation of the registration information for the following cycle of the optimisation process is output. This information comprises, for example, parameters which define the variation of a registration matrix (e.g. three angles defining the rotation and three translation parameters defining the shift) and is denoted by PAR in the figure. Based on the information PAR, the next cycle of the loop shown in FIG. 1 is started, e.g. by extracting N extracted images IEX.

Figure 3:
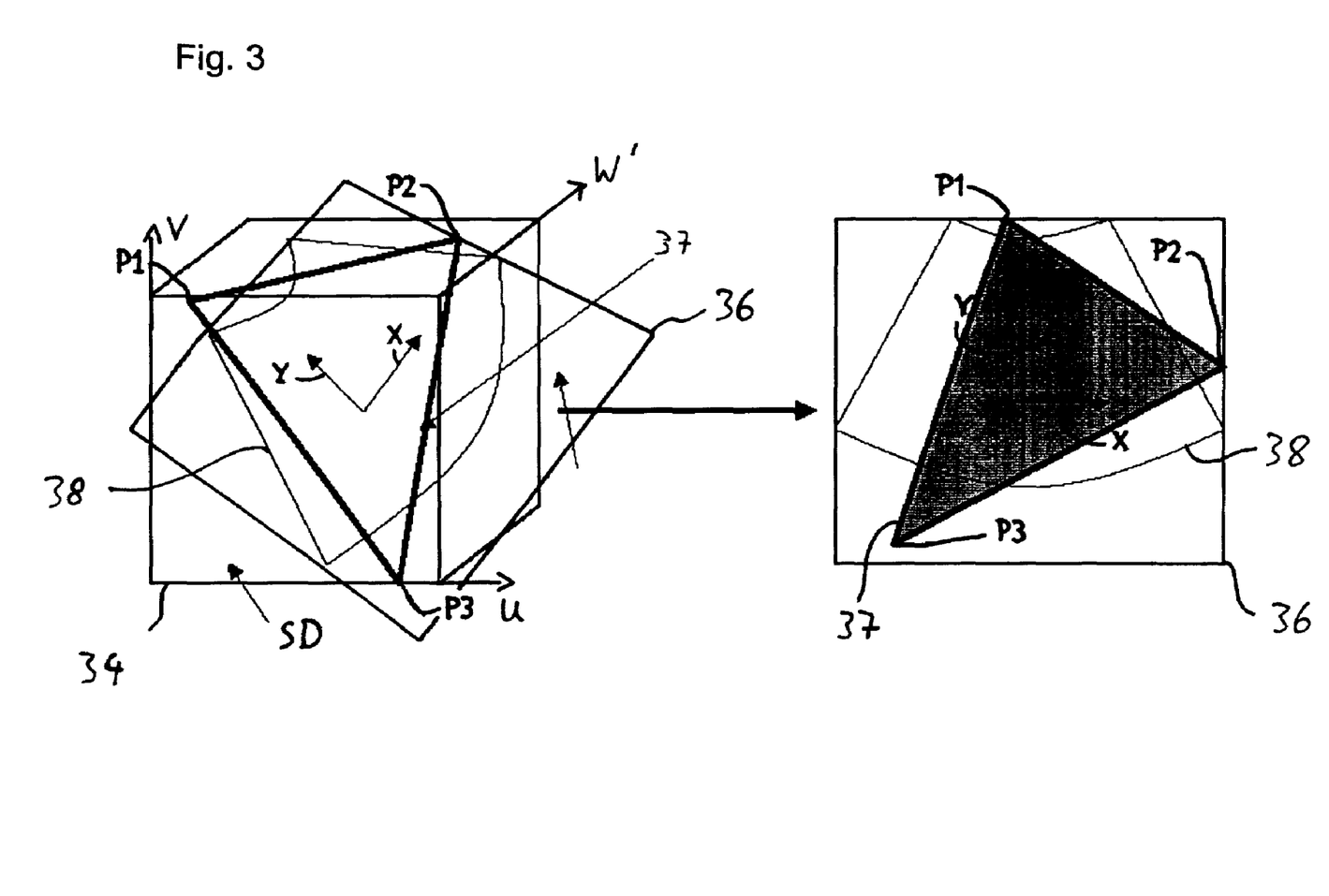
FIG. 3 a diagram illustrating the extraction of 2-D image data.

A preferred embodiment of the process of extracting a set of 2-D image data from the second (3-D) image data will be described in the following:

In FIG. 3, a cube 34 is shown which represents a volume of the second image data SD. For example, a grayscale value is assigned to each voxel (volume pixel) of the second image data SD inside the cube 34. At the beginning of the extraction process, registration information is used to determine a cut plane 36 of the second image data SD. The registration information defines an intermediate status of the registration. In other words: The goal of the process is to extract a set of 2-D image data in order to compare this set with a corresponding set of ultrasound image data, wherein it is assumed that the position and orientation of the two sets are the same. In order to define the cut plane 36, it is sufficient to use part of the registration information. However, the remaining part of the registration information is also necessary for the comparison of the two data sets. In particular, information about the rotation angle (with respect to an axis of rotation which extends perpendicularly to the cut plane 36) can be used during the extraction process or afterwards in order to prepare the (comparison of the two sets. Also, the position of the second image data SD (i.e. the position of a coordinate system of the data) and of the ultrasound image data with respect to the cut plane must be defined by the registration information. In practice, the registration information may be defined by a 3-D registration matrix which can be used to transform the coordinate system of the ultrasound image data to the coordinate system of the second image data. In particular, this transformation matrix can be used to determine the cut plane 36 by applying the transformation to the plane of the ultrasound image data to be compared. In this case, not only the position of the plane is defined, but the rotational state of the plane is also defined, i.e. the coordinate system of the plane cut plane is defined in relation to the ultrasound image data.

The area 38 within the common plane, for which relevant ultrasound image data exists, is also shown in FIG. 3. This area 38 has the typical shape of a windscreen wiper area and is located within the cut plane 36. In the example, the ultrasound image data have been obtained by a 2-D ultrasound detector. However, the invention is not limited to this type of detectors. Rather (in any embodiment of the invention), the ultrasound detector may be a detector which produces 3-D ultrasound image data. Alternatively, 3-D ultrasound image data may have been generated in a different manner, for example by scanning a volume using at least one 2-D and/or 3-D ultrasound detector and by calculating the 3-D ultrasound image data from the detector signals. Thus, the shape of the area of the 2-D ultrasound image data may differ from area 38. In particular, an optional intermediate step of processing the ultrasound image data may be performed before the comparison with the extracted set of second image data is performed: in this step, a region of interests may be defined by a user with respect to the second image data and/or with respect to the ultrasound image data. Correspondingly, arbitrary shapes may be defined.

Cutting the volume (here: the cube 34) of the second image data SD with the cut plane 36 produces the outlines of a cutting area 37, which is triangular in the example. More generally speaking, the cutting area might have a polygonal shape, wherein the edges of the polygon may be straight lines or curves. In any case, the procedure, which is described in the following, can be used.

The scanline procedure described in the following is particularly fast compared to traditionally applied procedures of obtaining data values within a defined (two-dimensional cutting) area. These traditional procedures include the transformation of each of the locations of the ultrasound image data into the coordinate system of the second image data, for example by applying the registration matrix.

The outcome of the cutting step is shown on the right-hand side of FIG. 3: the cutting area 37, which comprises three corners P1, P2, P3 and the ultrasound image data area 38 overlap each other and both are located within the cutting plane 36.

Figure 4:
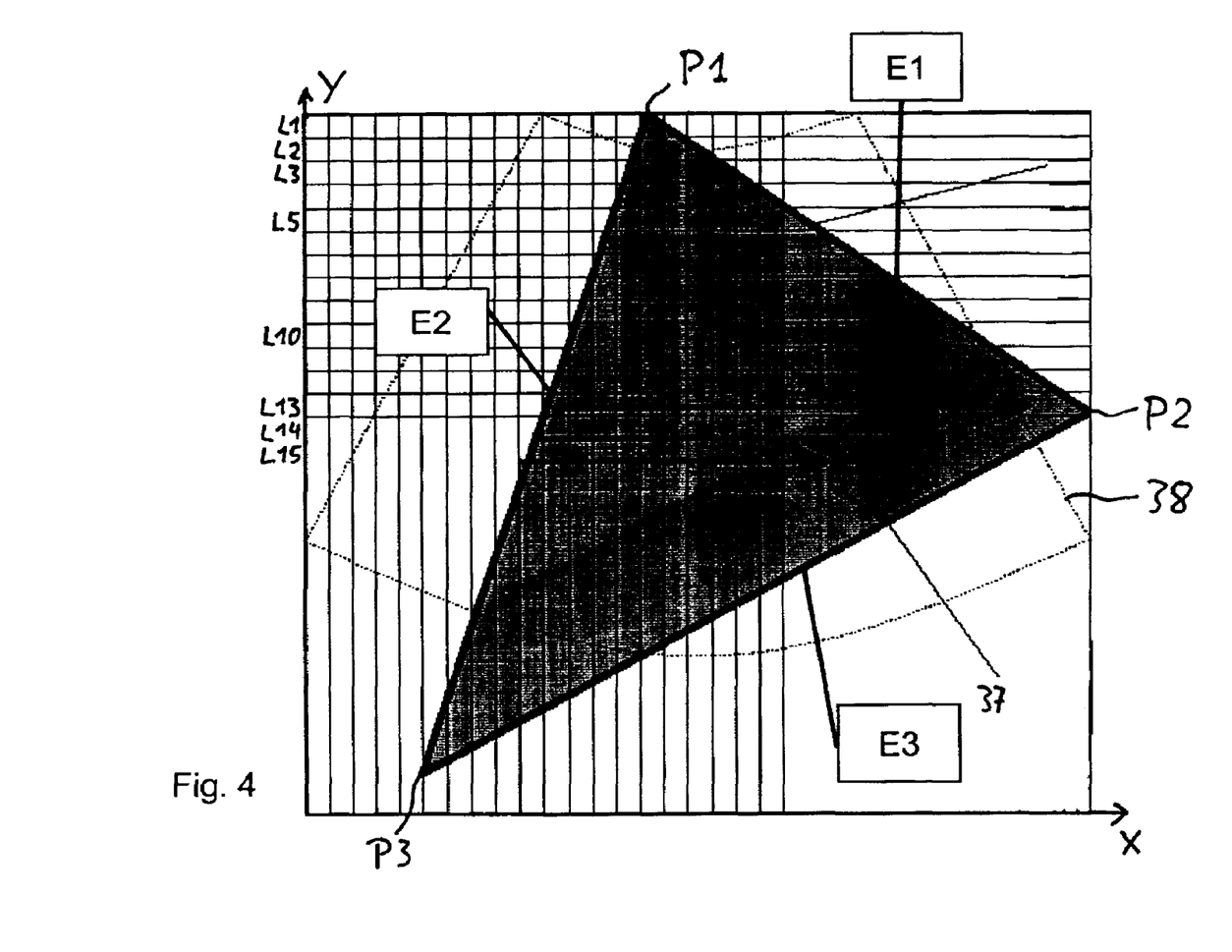
FIG. 4 a further diagram illustrating the extraction of 2-D image data.

The X-axis and the Y-axis of a Cartesian coordinate system of the ultrasound image data are shown in the FIGS. 3 and 4. The U-axis, the V-axis and a W'-axis (which is parallel to the W-axis of the coordinate system) of a Cartesian coordinate system of the second image data are shown in the left part of FIG. 3. The purpose of the scanline procedure is to determine the locations (e.g. voxels or points) within the coordinate system (U-V-W) of the second (3-D) image data for which image information is to be extracted.

Consecutive lines (or columns) in the X-Y coordinate system are scanned, starting and ending at the edges of the cutting area 37. The edges are of the noted by E1, E2, E3 in FIG. 4. In the example, each scanline starts at edge E2 (as indicated by arrows in lines L13, L14, L15). All scanlines which intersect the cutting area 37 are processed one after the other in consecutive order L1, L2, L3 ... in the same manner.

The corresponding coordinate values of the edges (i.e. the start and end points) of each scanline can be calculated easily, using the registration information. Then, the desired locations in each scanline are calculated by incrementing the coordinate values, starting at the start point of the scanline, from scan step to scan step by the same amount until the end point is reached. The locations are represented by squares in FIG. 4.

Details and alternative procedure elements of the scanline method are described in: J. D. Foley et al., "Computer Graphics—Principles and Practice", Chapter 3.6 "Filling Polygons", pages 92- 99, Addison-Wesley Publishing, Reading, Mass., ISBN-0201848406, April 2000. The content of these pages is herewith incorporated by reference.

The image values of the second image data which correspond to the locations identified in the scanline procedure (for example grayscale values), can now be determined. Depending on the desired precision of the extracted 2-D image data and depending on the existing spatial resolution of the second image data, the image values can be obtained by interpolation of values surrounding the identified location.

Since the scanline procedure is particularly fast, the fully automatic registration can be performed within a short period of time. Furthermore, it is possible to compare a large number of data sets and, therefore, to use a particularly reliable optimisation procedure in order to find the best values of the registration information. In particular, the optimisation procedure may re-start from different initial values of the registration information.

According to a preferred embodiment of the invention, a partially manual registration procedure may be used, which is described in European patent application 04 023 437.9 of the same inventors as this application, in order to obtain high-quality initial values of the registration information. In this procedure, a part of the registration process (partial registration) for registering the ultrasound image data and the second image data is performed automatically, so that the two coordinate systems are aligned with respect to one direction. In addition, a user may perform a further partial registration step, so that the two coordinate systems are aligned with respect to a further direction. The result of the partially manual registration procedure is registration information which is used as initial values for the procedure according to the present invention.

The invention claimed is:

1. A method of registering ultrasound image data of an object (3) and second image data (SD) of the object (3), wherein the second image data (SD) are three-dimensional (3-D) image data and wherein the method comprises the steps:
   obtaining sets (first sets) of the ultrasound image data, wherein each set of ultrasound image data consists of ultrasound image data of locations within a single plane (36) of a coordinate system (X-Y) of the ultrasound image data (ultrasound coordinate system);
   extracting sets (second sets) of 2-D image data from the second image data (SD), wherein each set of 2-D image data consists of image data of locations within a single cut plane (36) of a coordinate system (U-V-W) of the second image data;
   comparing one of the first sets with one of the second sets and automatically generating a measure of similarity between the first set and the second set; and
   optimising the similarity by varying the first set and/or the second set to be compared.

2. The method of claim 1 wherein registration information, which defines a registration of the ultrasound coordinate system and of the coordinate system of the second image data, is determined according to an optimised pair of data sets, wherein the optimised pair comprises the first set and the second set having an optimum similarity.

3. The method of claim 1 wherein the single cut plane (36) of the coordinate system (U-V-W) of the second image data is chosen to be equal to the single plane (36) of the ultrasound coordinate system, based on instantaneous values of registration information which defines a registration of the ultrasound coordinate system (X-Y) and of the coordinate system (U-V-W) of the second image data.

4. The method of claim 1 wherein in the step of comparing one of the first sets with one of the second sets a plurality of pairs are compared and a measure of similarity is calculated for each of the pairs, wherein each of the pairs comprises one of the first sets and one of the second sets, wherein all of the pairs correspond to the same geometrical transformation for transforming the ultrasound coordinate system (X-Y) into the coordinate system (U-V-W) of the second image data, or vice versa, and wherein the measures of similarity of all of the pairs are combined and optimised by varying the first sets of the pairs and/or the second sets of the pairs in a geometrically corresponding manner.

5. The method of claim 1 wherein, in the step of extracting at least one of the second sets, a plurality of locations of the 2-D image data are determined, wherein the locations are located in a straight line in the cut plane (36) and wherein end locations of the straight line, which define end points of the straight line at opposite ends, are determined by transforming corresponding locations in the ultrasound coordinate system (X-Y) into the coordinate system (U-V-W) of the second image data.

6. The method of claim 1 wherein the locations between the opposite end locations are determined in consecutive order along the straight line.

7. An arrangement (2) for registering ultrasound image data of an object (3) and second image data of the object (3), wherein the second image data are three-dimensional (3-D) image data and wherein the apparatus comprises:

a data storage (4) for storing the second image data and/or an interface for receiving the second image data; and a registration device (25) which is adapted to combine the ultrasound image data and the second image data; characterized in that the registration device (25) comprises:

a dataset extraction unit (41) which is adapted to extract sets of 2-D image data from the second image data, wherein each set of 2-D image data consists of image data of locations within a single cut plane of a coordinate system of the second image data;

a dataset comparison unit (42) which is connected to the dataset extraction unit (41) and which is adapted to compare at least one of the sets of 2-D image data with at least one set of ultrasound image data, wherein each set of ultrasound image data consists of ultrasound image data of locations within a single plane of a coordinate system of the ultrasound image data; and an optimisation unit (43) which is connected to the dataset comparison unit (42) and which is adapted to optimise registration information (R), wherein the registration information (R) is based on a comparison result of the dataset comparison unit (42).

* * * * *